(12) United States Patent
Broennimann et al.

(10) Patent No.: US 7,169,133 B2
(45) Date of Patent: Jan. 30, 2007

(54) INJECTION DEVICE WITH LOCKABLE DOSING MEMBER

(75) Inventors: Lorenz Broennimann, Burgdorf (CH); Fritz Kirchhofer, Sumiswald (CH)

(73) Assignee: TecPharma Licensing AG, Burgdorf (CH)

( * ) Notice: Subject to any disclaimer, the term of this patent is extended or adjusted under 35 U.S.C. 154(b) by 0 days.

(21) Appl. No.: 11/046,552

(22) Filed: Jan. 28, 2005

(65) Prior Publication Data

US 2005/0177115 A1 Aug. 11, 2005

(30) Foreign Application Priority Data

Jan. 28, 2004 (DE) .................. 10 2004 004 310

(51) Int. Cl.
*A61M 5/00* (2006.01)
(52) U.S. Cl. ..................................... 604/208
(58) Field of Classification Search ................ 604/208
See application file for complete search history.

(56) References Cited

U.S. PATENT DOCUMENTS 5,084,017 A * 1/1992 Maffetone .................. 604/110
5,514,097 A * 5/1996 Knauer ....................... 604/136
5,807,346 A * 9/1998 Frezza ........................ 604/208
6,086,567 A * 7/2000 Kirchhofer et al. ......... 604/211
6,319,234 B1 * 11/2001 Restelli et al. .............. 604/198

FOREIGN PATENT DOCUMENTS

DE 199 45 397 C3 7/2001
EP 0 713 403 B1 12/1999

* cited by examiner

*Primary Examiner*—Nicholas D. Lucchesi
*Assistant Examiner*—Laura A. Bouchelle
(74) *Attorney, Agent, or Firm*—Dorsey & Whitney, LLP

(57) ABSTRACT

An injection device including a housing, a reservoir for a product to be injected, an advancing apparatus that carries out an advancing movement to discharge a selected dose of product from the reservoir, a dosing member that carries out a propulsion movement relative to the housing in a propulsion direction and a dosing movement counter to the propulsion direction, the dosing member operably coupled with the advancing apparatus such that the propulsion movement causes the advancing movement of the advancing apparatus, wherein the length of a distance determining the discharged dose is selected by the dosing movement, a first catch mechanism formed by the housing in a sleeve section that surrounds the dosing member, and a second catch mechanism formed by one of the dosing member or a separate, additional dosing catch body, wherein a catch engagement of the catch mechanisms is releasable through a rotation free dosing movement of the dosing member or the separate, additional dosing catch body.

19 Claims, 9 Drawing Sheets

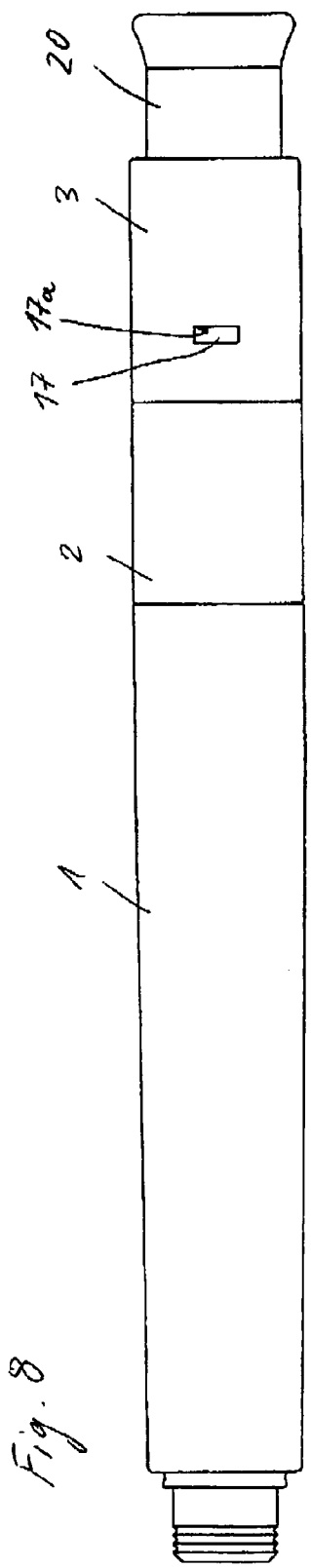
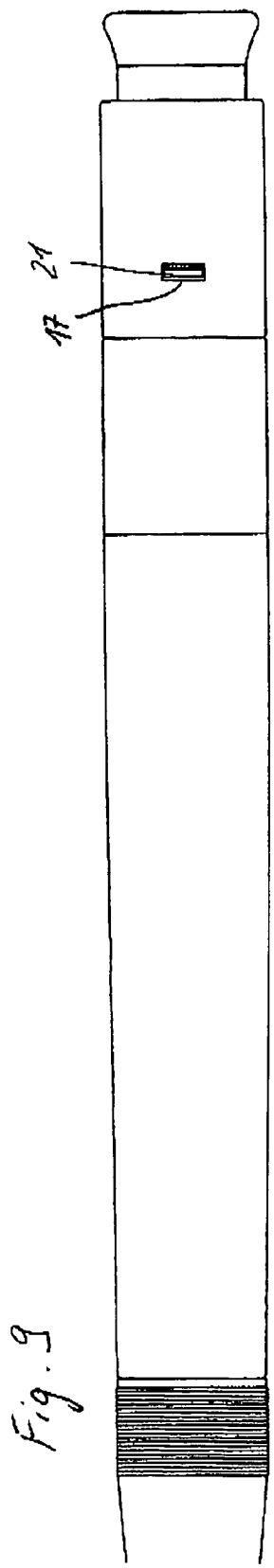
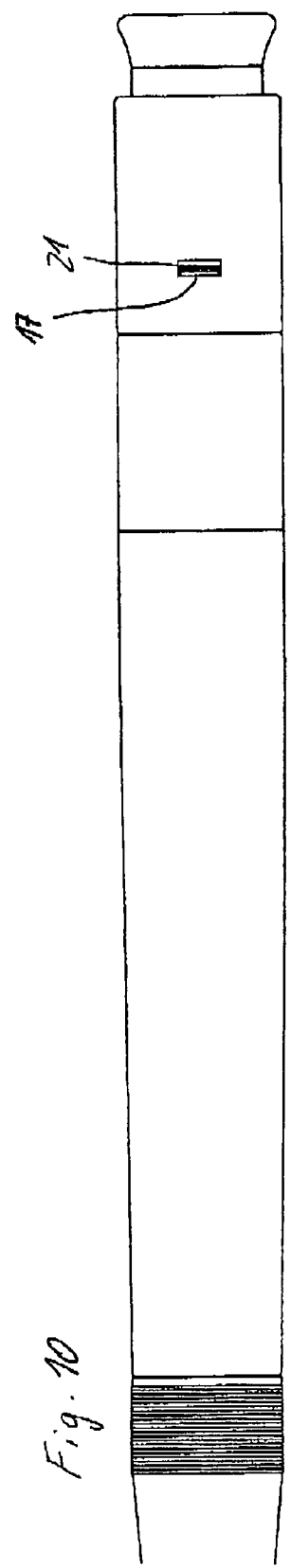

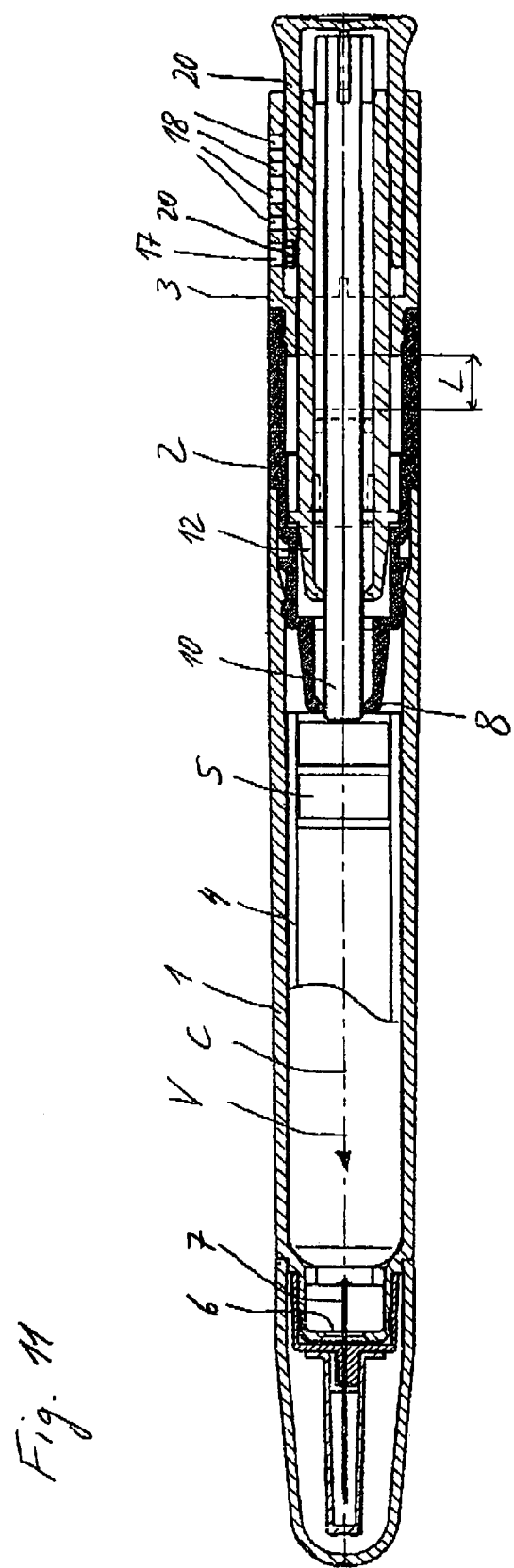

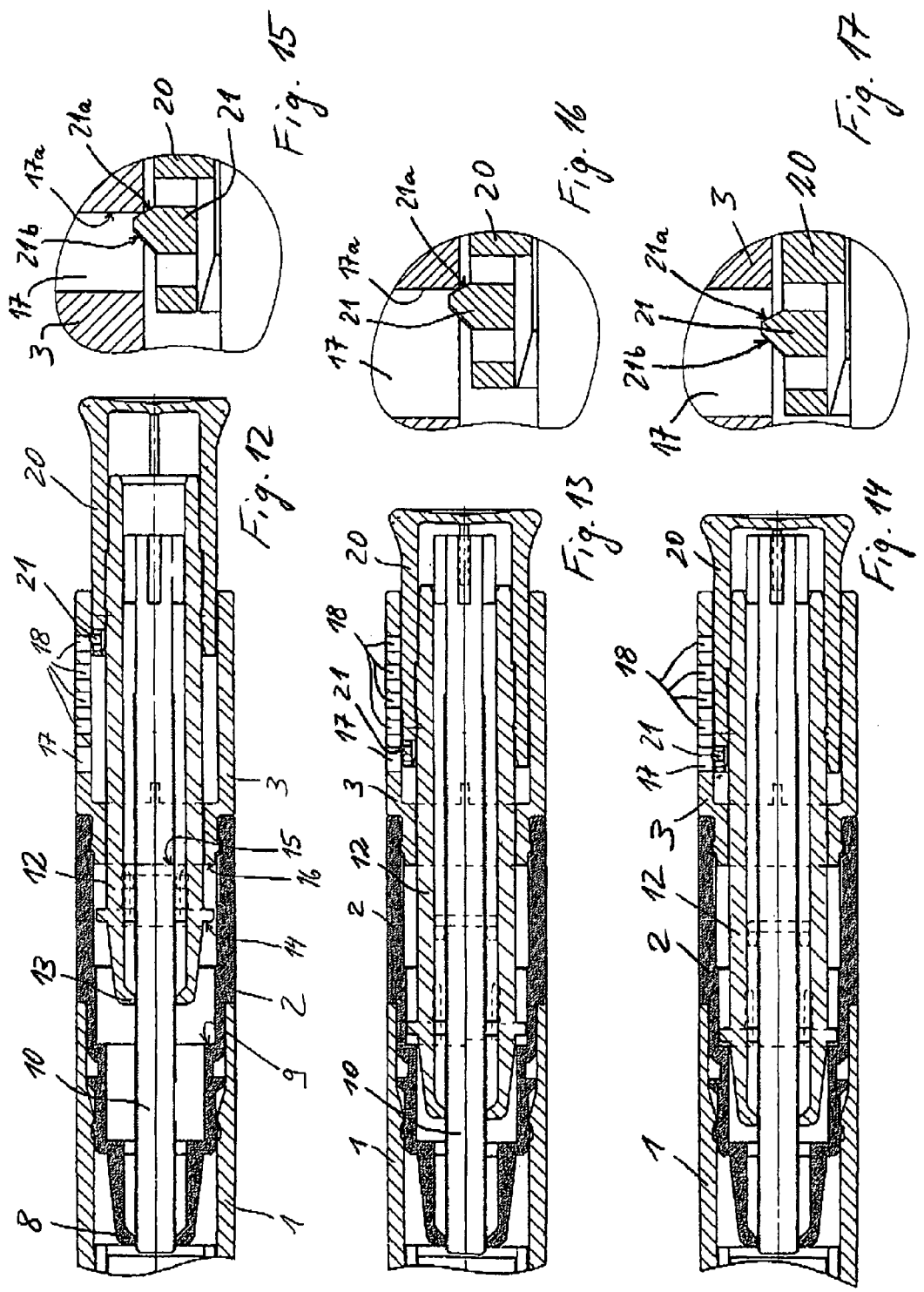

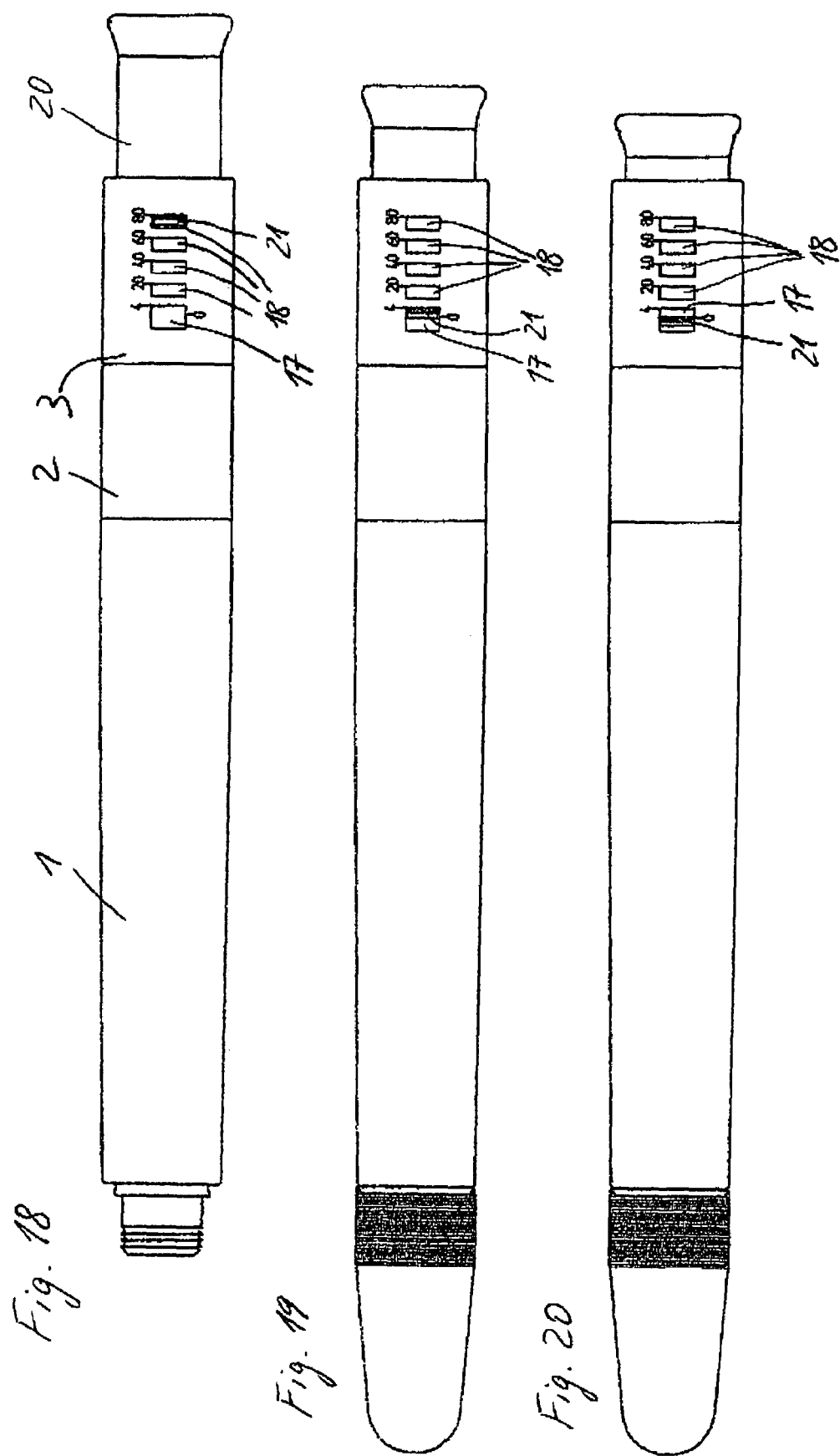

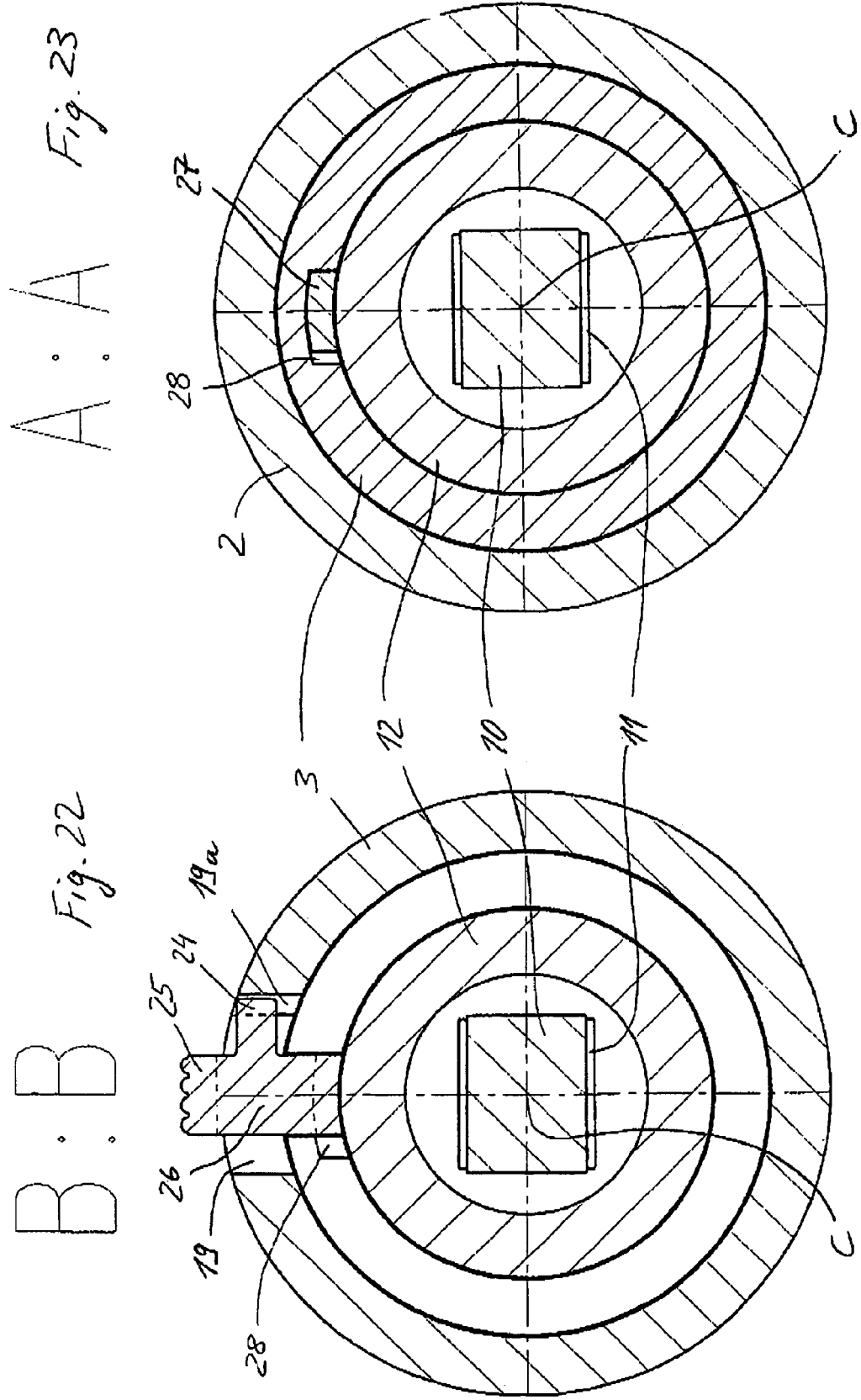

INJECTION DEVICE WITH LOCKABLE DOSING MEMBER

CROSS-REFERENCE TO RELATED APPLICATION

This application claims priority to German Application No. 102 004 004 310.8, filed on Jan. 28, 2004, the contents of which is incorporated by reference herein in its entirety.

BACKGROUND

The invention relates to injection devices and methods, including, an injection device that comprises a lockable dosing member for the dosed administration of an injectable product. In some embodiments, the injection device particularly serves the self-administration of the product. Preferably, it serves the administration of a parathyroid hormone, for example heparin, in the treatment of osteoporosis. However, a device in accordance with the present invention can also be used in other therapies, for example for the administration of insulin in diabetes therapy. In some preferred embodiments, the injection device has overall the shape of a pen.

Not least due to their comfortably manipulable shape, injection pens are widely used especially in the self-administration of medicaments. In self-administration, simple manipulability, precision and certainty in dosing, along with the lowest possible price of the device, become of great importance.

WO 02/30495 A2 discloses an injection pen developed specifically for osteoporosis therapy. The medicament is conveyed from an ampoule by means of a piston. The driving of the piston is effected by mean of a piston rod, which is held in a housing of the pen so as to be axially displaceable in a straight manner. The medicament, as is normally the case with injection pens, is discharged by a propulsion stroke carried out in common by the piston rod and the piston. The length of the stroke determines the dose administered each time the medicament is discharged. The setting of the dose is the function of a dosing member, which together with the piston rod forms a spindle drive. Through a rotary movement of the dosing member, the length of the propulsion stroke is adjusted.

For the setting of the dose, in a first step, the dosing member must be rotated into a first catch engagement, in which it is locked with the housing in a zero dose position and from which the dose can be adjusted in a next step.

In order to exhaust the air from the product-guiding parts of the pen before an administration, for example after an ampoule change or a refilling of the ampoule, i.e., in order to perform a priming, the dosing member can be rotated out of the zero dose position and, instead of being moved to a fixed end stop that defines a maximum dose, rather may be moved into a priming position by means of a relatively short dosing rotary movement. In the priming position, it is in a second catch engagement with the housing.

The dosing rotary movement of the dosing member effects, via an appropriate coupling to the housing and by virtue of the straight guiding of the piston rod, a superimposed backward movement of the dosing member relative to the housing and relative to the piston rod.

The catch mechanism is formed by axially-extending V-grooves formed in regular distribution over an outer peripheral surface of the dosing member, which grooves are engaged from the outside by a finger formed by the housing. The finger is elastically bendable in a radially-outward manner and, during the dosing rotary movement, snaps from one V-groove into another. For the adjustment of the dose, the finger must first click into the longest of the V-grooves, so that the dosing member assumes a zero dose position, from which it can then carry out a first, purely translational backward movement with the finger engaging the V-groove, which movement brings the dosing member into engagement with a thread formed on the housing. Only the engagement with this thread causes the axial backward movement required for the adjustment of the discharge stroke to be superimposed by the dosing rotary movement of the dosing member. The dosing mechanism meets the requirements placed on it from a functional point of view, but is very complex.

Another injection pen with lockable dosing member is known from WO 96/07443 A1. In this pen, the dose is adjusted by means of a dosing rotary movement of the dosing member, on which movement an axial translational movement is superimposed. With the aid of a catch mechanism between the dosing member and a latch attached in a hinged manner to the housing of the pen, different doses can be set. The catch mechanism serves in the first instance to secure the dosing member in the zero dose position. The dosing member is provided on an outer peripheral surface with grooves arranged axially in a row. The latch can form a catch engagement with each of these grooves by snapping forth into the respective groove. In order to be able to withdraw the dosing member out of the housing of the pen from the zero dose position into a proximal end position, the latch must be operated. From the proximal end position, the desired dose can be set in that, through the dosing rotary movement, the dosing member is turned back again in the distal direction, i.e., into the housing, by a desired path length along a spindle. During this dosing rotary movement, the catching of the latch in the grooves of the dosing member produces an audible clicking and, in addition, offers a certain security against an inadvertent rotation of the dosing member. However, this known dosing mechanism is quite complex, and the latch attached to the outside of the housing may cause problems.

SUMMARY

It is an object of the invention to provide an injection device having dose adjustment through a lockable dosing member that is simple and certain with respect to the dosing, and is nevertheless economical.

In one embodiment, the invention relates to an injection device that comprises a housing, a reservoir for a product to be injected, a advancing apparatus, and a dosing member.

In one embodiment, the present invention comprises an injection device, and method of its manufacture and use, wherein the device comprises a housing, a reservoir for a product to be injected, an advancing apparatus that carries out an advancing movement to discharge a selected dose of product from the reservoir, a dosing member that carries out a propulsion movement relative to the housing in a propulsion direction and a dosing movement counter to the propulsion direction, the dosing member operably coupled with the advancing apparatus such that the propulsion movement causes the advancing movement of the advancing apparatus, wherein the length of a distance determining the discharged dose is selected by the dosing movement, a first catch mechanism formed by the housing in a sleeve section that surrounds the dosing member, and a second catch mechanism formed by one of the dosing member or a separate, additional dosing catch body, wherein a catch engagement of the catch mechanisms is releasable through a rotation free dosing movement of the dosing member or the separate, additional dosing catch body.

In one embodiment, the injection device preferably has the shape of a pen. The housing can directly form the reservoir. Preferably, however, the housing receives a receptacle that forms the reservoir, optimally in the form of an ampoule. The product is preferably a medicament fluid, but can also consist of a product having exclusively cosmetic effects. The advancing apparatus acts on the product located in the reservoir and carries out a propulsion movement in order to discharge the product. The magnitude of the advancing movement, preferably an axial piston stroke, is determined through a pre-adjustment of the dosing member. The dosing member carries out, relative to the housing, a propulsion movement in a propulsion direction and dosing movement opposite to the propulsion direction. It is coupled to the advancing apparatus such that the propulsion movement produces the advancing movement of the advancing apparatus. Through the dosing movement, the length of distance determining the dose to be discharged, which is the distance that the dosing member can cover in its propulsion movement, is adjusted. This corresponds to the pre-adjustment mentioned in connection with the advancing apparatus.

For the adjustment of the dose, the dosing member and the housing each form a catch mechanism. A catch engagement of the two catch devices is, according to the present invention, releasable through a rotary-movement free dosing movement of the dosing member or of a separate dosing catch body that works in conjunction with dosing member for the dosing. The rotary-movement free dosing movement considerably simplifies the support of the dosing member and/or of the dosing catch body by the housing and the coupling of the dosing member to the advancing apparatus. The dosing movement can advantageously be a linear axial movement, which preferably also applies to the propulsion movement of the dosing member. It suffices, however, that the housing and the dosing member are in simple sliding contact directly with each other or via an element moved in unison, in one preferred case, a linear guide.

The coupling of the dosing member with the advancing apparatus can, with respect to the propulsion movement, advantageously be a simple take-along engagement, i.e., an engagement that produces the slip-free moving of an advancing element of the advancing apparatus, namely a drive or driven element, or preferably, the advancing apparatus as a whole, when the dosing member carries out its propulsion movement. The coupling with the advancing apparatus consequently need not produce the dosing movement of the dosing member as a superimposed rotational and translational movement, for example via a spindle drive as in the prior art. Rather, it is sufficient that the dosing member is simply uncoupled from the advancing apparatus during the carrying out of its dosing movement. The coupling between the dosing member and the advancing apparatus can advantageously be formed, for example, as a simple toothed engagement in the manner of a ratchet, as this is known from toothed-type rack pens.

In one embodiment, the housing forms its catch mechanism for the dosing catch engagement with the dosing member in a housing sleeve element surrounding the dosing member. This catch mechanism is thus an integral part of the housing and not attached to the exterior of the housing, possibly via an articulated joint, as is the case with the housing-side catch mechanism of the injection device in WO 96/07443 A1. In the following description, the catch mechanism of the housing is designated the first catch mechanism and that of the dosing member, to note the distinction, is called the second catch mechanism.

In some embodiments, the first catch mechanism is preferably formed directly in the original molding on the respective housing section, i.e., as one piece with the housing sleeve section. A preferred method of the original molding is injection molding in plastic. However, it should not be ruled out that the first catch mechanism may be formed separately from the housing sleeve section, then attached to the housing sleeve section, not in an articulated, but rather in a fixed manner, whereby in comparison to an articulated attachment the costs are still reduced, as well as the susceptibility to failure.

In order to be able to release the dosing catch engagement, the first and the second catch mechanisms can each be elastically pliant. However, in some embodiments, it is preferable that only one of the two catch mechanisms is elastically pliant and the other not pliant. Preferably, the first catch mechanism is not pliant, and the second catch device elastically yields to it during the releasing of the dosing catch engagement. Alternatively, the first catch mechanism can instead be designed as elastically pliant and the second catch mechanism as not pliant. In the case of the pliancy of the second catch mechanism, preferably radially to the direction of the dosing movement, an optical indication of the dose position of the dosing member can be obtained at the same time.

In some embodiments, the first catch mechanism preferably forms, in a jacket of the sleeve section, at least one catch surface pointing in the propulsion or injection direction. The second cast mechanism, in the dosing catch engagement, grasps behind the at least one catch surface of the first catch mechanism. The formation of the at least one catch surface in the jacket of the housing sleeve section is advantageous not least because such a catch surface uses no additional space to the outside beyond the jacket thickness and thus produces no thickening of the injection device. This arrangement promotes an advantageously slender shape of the injection device. If the at least one catch surface is not formed in the jacket of the housing sleeve section, but rather projects inwardly from a jacket inner surface or outwardly from a jacket outer surface, then a catch surface projecting inwardly from the jacket inner surface is preferable to a catch surface projecting outwardly from a jacket outer surface. If the first catch mechanism displays several catch surfaces in order to be able to set several different doses, then the several catch surfaces are arranged spaced apart in a row in the propulsion direction and preferably formed in the same manner as the previously-mentioned at least one catch surface.

In a preferred embodiment, the at least one catch surface forms a boundary wall of a cutout in the jacket of the housing sleeve section, and in some preferred embodiments, a proximal boundary wall. A catch element of the second catch mechanism projects into the cutout, in order to grasp behind the at least one catch surface in the dosing catch engagement. The catch element that grasps behind is preferably visible from the outside, so that the dose position of the dosing member can be immediately seen by means of the dosing catch engagement. For such a sight control, the housing sleeve section forming the first catch mechanism can be produced from a transparent material. In some embodiments it may be preferable, however, that a catch element of the second catch mechanism is visible only in the dosing catch engagement and is otherwise covered. In such embodiments, the mentioned cutout in the housing sleeve section is formed as a perforation. The perforation can be covered from the outside by a transparent material or can be simply left open.

The dose position of the dosing member can, in addition, be advantageously read from a dose scale. The dose scale can be applied to the dosing member. However, in some embodiments, a dose scale is preferably applied to the housing directly at the first catch mechanism. The mentioned catch element of the second catch mechanism advantageously forms at the same time the single pointer or, if need be, one of several pointers of a dose indicator thus formed.

In preferred embodiments, in which the second catch mechanism is elastically pliant for the releasing of the catch engagement, the second catch mechanism snaps radially outward, in relation to a central longitudinal axis, into the dose catch engagement. In another embodiment, the second catch mechanism snaps in the peripheral direction of the sleeve section of the housing, which forms the first catch mechanism, into the dosing catch engagement.

In some embodiments, the second catch mechanism is formed as one piece on the dosing member. During the original formation of the dosing member, preferably in the plastic injection molding. In another, likewise preferred embodiment, the second catch mechanism is obtained by a separately produced catch body movably supported by the housing, preferably axial guided, and through the fact that this separate catch body is movable relative to the housing and relative to the dosing member in and out of the catch engagement. A separately produced catch body can also be attached to the dosing member or be firmly connected to the dosing member at least in the assembled state of the injection device, in which case the attachment allows elastic yielding.

In preferred embodiments, the dosing catch engagement makes possible the setting of a small product dose, predetermined through the dosing catch engagement, in order to be able to prime the injection device in a defined manner. A priming of the injection device is always necessary when the reservoir is refilled or exchanged altogether, namely, in order to de-aerate the product-conducting parts of the injection device through the discharging of a small product dose and, at the same time, to ensure normal functioning. The dosing movement for the setting of such a priming dose is substantially smaller that a maximum length of the dosing movement, which the dosing member can carry out for the setting of a maximum dose.

In some embodiments, the settable maximum dose is preferably predetermined through a fixed end stop, in other words not through the dosing catch engagement. The pre-determination of the end stop for the maximum dose can, however, also be prescribed as a catch position in the dosing catch engagement; this catch engagement should safely prevent the dosing member from carrying out a dosing movement beyond the maximum dose position. The fact that the distance that the dosing member can travel from a starting position to the priming position is significantly shorter than the maximum distance that can be covered to the maximum dose position means that the maximum coverable distance is longer by a multiple than the distance that can be covered by moving to the priming position. In this context, a multiple does not mean it is necessarily a matter of a whole-number multiple. Typically, the maximum coverable distance is at least ten times as long as the distance up to the priming position. The starting position, to which the coverable distance is relative, is the zero dose position. Preferably, the ratios hold true also in relation to each additional dose position into which the dosing member can be locked between the zero dose position and the maximum dose position, if it is the case that different doses per catch engagement can be set.

In some embodiments, the advancing apparatus preferably comprises a piston and a piston rod acting on the piston in the propulsion or injection, dispensing or administration direction, which piston rod can be fixedly connected to the piston, but preferably only presses against the piston in the propulsion direction. The piston rod can, in particular, consist of a toothed rack or, for example, a piston rod that, in the manner of a toothed rack, only works in conjunction with a drive element that drives it, preferably a carrier. Such a piston rod acting in the manner of a toothed rack is known from DE 199 45 397 C2, which is incorporated herein by reference.

In some embodiments, for the realization of the priming function, the catch engagement between the dosing member and the housing is preferably formed such that between the at least one catch surface and the grasping-behind catch element there remains a clear gap, measured in the propulsion direction, which gap corresponds to the distance covered in the catch engagement for the priming. The clear gap or distance corresponds at least to a selectable dose unit, preferably a few dose units, for example 2, 3, or 4 dose units.

It is advantageous for priming that the coupling between the dosing member and the advancing apparatus is formed such that the dosing member performs the dosing movement in relation to the advancing apparatus from the zero dose position into the priming position in a slip-free manner. In this instance, the dosing member and the advancing apparatus in the zero dose position and in the priming position are, in each case, determined with respect to each other such that a movement of the dosing member in the propulsion direction relative to the advancing direction is not possible. This advancing is advantageously performed by toothed couplings, as these are known from toothed rack pens. One preferred advancing apparatus is known from DE 199 45 397 C2, to which reference may be made, for the coupling of a dosing member and a piston rod, since the carrier in that document forms a dosing member generally useful in the present invention. Through the coupling with the advancing apparatus, an undesired movement of the dosing member relative to the advancing apparatus from the priming position in the propulsion direction is consequently prevented, which the dosing engagement would absolutely permit, while on the other hand the catch surface of the housing sleeve section in the priming position forms a stop acting counter to the propulsion direction for the catch element of the dosing member. The elastic force necessary for the releasing of the dosing catch engagement must, for the fulfillment of the priming position, attain a magnitude that can be definitely felt by the user.

The priming function according to the present invention can also be designed in combination with a dosing member exhibiting a dosing movement is a rotary movement or includes a rotary movement. Preferred dosing members of this type are described in DE 199 00 792 C1 and WO 97/36625, to which reference is made in this context. Such dosing members form an axial-position changeable stop for a lifting movement of the carrier of the advancing apparatus.

In some embodiments, the elastic pliancy can be obtained through material elasticity, or one of the two catch mechanisms or, if necessary, both catch mechanisms, may have elasticity of shape. In some embodiments, a bending elasticity is suitable. For the attainment of a priming function, the elastic force to be overcome and the shape of the catch element and/or of the catch surface forming the stop surface are in combination finely calibrated to each other.

BRIEF DESCRIPTION OF THE DRAWINGS

FIG. 8 shows the injection device of FIG. 1 in a plan view of a catch mechanism of a housing of the injection device, wherein the dosing member assumes the maximum dose position, FIG. 9 shows the plan view of FIG. 8, wherein the dosing member assumes the priming position, FIG. 10 shows the plan view of FIG. 8, wherein the dosing member assumes the zero dose position, FIG. 11 shows an injection device according to a second exemplary embodiment, FIG. 12 shows the injection device of FIG. 11 in a state in which a dosing member of the injection device assumes a maximum dose position, FIG. 13 shows the injection device of FIG. 11 in a state in which the dosing member assumes a priming position, FIG. 14 shows the injection device of FIG. 11 in a state in which the dosing member assumes a zero dose position, FIG. 15 shows a catch mechanism of the dosing member in detail in the maximum dose position, FIG. 16 shows the catch mechanism of the dosing member in the priming position, FIG. 17 shows the catch mechanism of the dosing member in the zero dose position, FIG. 18 shows the injection device of FIG. 11 in a plan view of a catch mechanism of the housing of the injection device, wherein the dosing member assumes the maximum dose position, FIG. 19 shows a plan view of FIG. 18, wherein the dosing member assumes the priming position, FIG. 20 shows a plan view of FIG. 18, wherein the dosing member assumes the zero dose position, FIG. 22 shows a section drawn along line A—A of FIG. 21, FIG. 23 shows a section drawn along line B—B of FIG. 21.

DETAILED DESCRIPTION OF THE DRAWINGS

Figure 1:
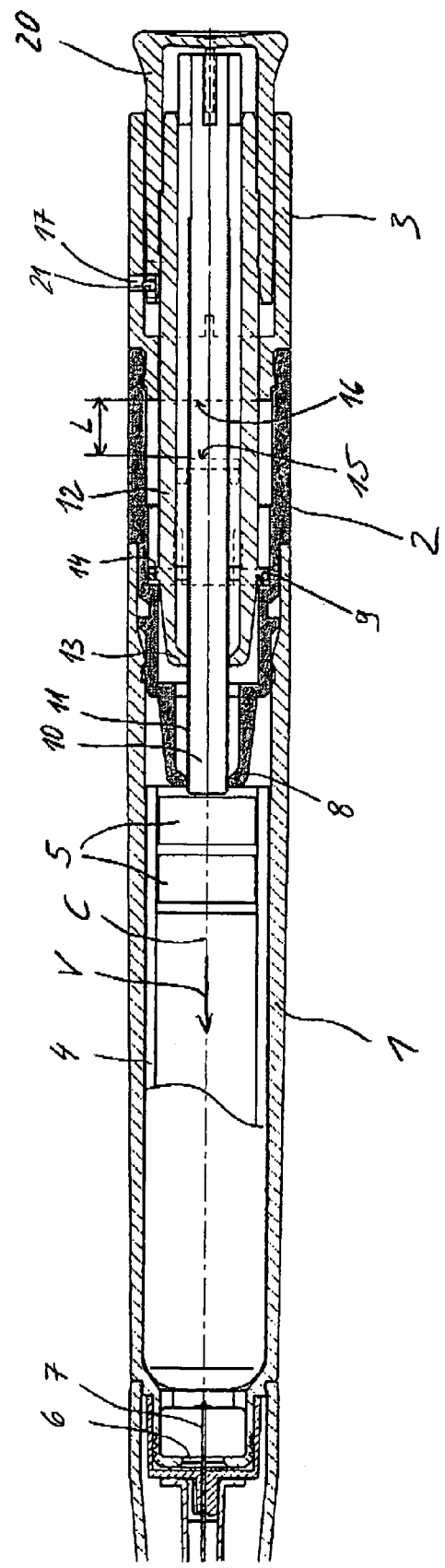
FIG. 1 shows an injection device according to one exemplary embodiment of the present invention.

FIG. 1 shows an injection device according to a first embodiment example in a longitudinal section along a central axis C. The injection device is formed as a toothed rack pen and particularly serves the administration of a medicament for the treatment of osteoporosis. The dose administered per injection is always the same. Indeed the injection device makes available a sufficient amount of the product to be able to discharge and administer this always-constant dose several times. In addition to the setting and discharging of the always-constant dose to be administered, in the following called the maximum dose, the injection device is also equipped with a priming function, in order to be able to de-aerate the product-conducting parts of the injection device in a reliable manner, but with the minimum possible loss of medicament.

The injection device exhibits a housing that is formed of three pieces, a distal sleeve section 1, a middle sleeve section 2 and a proximal sleeve section 3, which, in each case, are concentric to the common central longitudinal axis C. In the distal sleeve section 1, a reservoir 4 is provided in the form of an ampoule. A piston 5 closes off the reservoir 4 at its distal end in a liquid-tight manner. The piston 5 is received in the reservoir 4, being movable axially along the longitudinal axis C in a propulsion direction V. At its proximal end the reservoir 4 exhibits an outlet 6 that is closed off by a sealing element. An injection cannula 7 projects through the sealing element. The injection cannula 7 is attached in a cannula holder that is affixed to the distal end of the sleeve section 1. With the affixing a proximal section of the injection cannula 7 penetrates the sealing element at the reservoir outlet 6. A first protective cap is placed onto the cannula holder, which protects against penetration damage during the placing on of the injection cannula 7. Furthermore, an external cap is placed onto the sleeve section 1, which cap, after the removal of the first protective cap likewise protects against penetration damage from the freely jutting cannula section of the injection cannula 7 present after removal of the first protective cap.

The piston 5 is connected to a piston rod 10, which projects axially from the proximal end of the piston 5 in the proximal direction. The piston rod 10 presses only loosely in the propulsion direction V against the piston 5, in order to push it in the reservoir 4 in the propulsion direction V. In the depicted embodiment, a fixed connection does not exist. However, it would likewise be possible to fixedly connect the piston 5 and the piston rod 10. The piston 5 and the piston rod 10 form an advancing mechanism with the piston 5 as the driven member and the piston rod 10 as the driving member. The piston rod 10 is a toothed rack with at least one, preferably several, tooth rows. In the embodiment example it shows two tooth rows 11 lying diametrically opposite each other and extending axially. Further, it is provided with at least one axially extended engagement mechanism, for example a flattening, which serves the straight guidance of the piston rod 10 in the propulsion direction V. The engagement mechanism serving the straight guidance extends at least over such an axial length of the piston rod 10 that the piston rod 10 is guided in a axially straight manner over its entire translation path. In the embodiment example the piston rod 10 exhibits on both longitudinal sides in each case a flattening between the teeth rows 11 over the axial length of both tooth rows 11.

The piston rod 10 is mounted in the housing in such a way that it can be moved relative to the housing only in the driving direction V. The middle housing section 2 in the form of two blocking elements 8 forms the engagement means required for this. Each of the blocking elements 8 engages one of the rows of teeth 11. The teeth of the tooth rows 11 are formed asymmetrically with respect to the propulsion direction V such that the blocking engagement between the two blocking elements 8 and the tooth rows 11 allows movement of the piston rod 10 in the propulsion direction V, but prevents movement against the propulsion direction V. In the embodiment example the tooth rows 11 are designed as sawtooth rows with appropriate orientation of the saw teeth.

At the proximal end a dosing member juts out from the housing. The dosing member is in two parts, comprising a carrier 12 and a dosing knob 20. The carrier 12 and the dosing knob 20 are connected to each other such that they can execute no movement relative to each other, in particular in or against the forward drive direction V. They are both concentric to the longitudinal axis C. The dosing knob 20 is attached to the proximal end of the carrier 12 and is connected in an interlocking manner to the carrier 12 in such a way that the said axial relative movement cannot take place and furthermore no rotational movement around the longitudinal axis C can take place between the carrier 12 and the dosing knob 20. In this embodiment, the carrier 12 and the dosing knob 20 form a physically and functionally integrated dosing member.

The middle housing section 2 guides the dosing member axially linearly by slide guidance. The dosing member is coupled with the advancing mechanism by means of tooth engagement, the carrier 12 engaging the tooth rows 11. The tooth engagement is the same as the tooth engagement of the blocking element 8. For the tooth engagement the carrier element 12 forms two carrier elements 13, which at their distal ends project finger-like in the propulsion direction, engage the tooth row 11 and, by the way as with the blocking elements 8, are elastically bendable radially outward out of engagement. The tooth engagement is designed such that the dosing member cannot be moved relative to the piston rod 10 in the propulsion direction V, but on the other hand, due to the ability of the carrier elements 13 to yield elastically, can be moved against the forward drive direction V relative to the piston rod 10. In the movement against the propulsion direction V the carrier elements 13 slide over the tooth rows 11. The medicament dose is adjusted through the movement of the dosing member against the propulsion direction, the dose being ejected by a final forward movement, which the dosing member carries out in common with the advancing mechanism.

In the initial position of the dosing member, shown in FIG. 1, the dosing member assumes a zero dose position relative to the housing, i.e., a farthest forward position in the propulsion direction V, in which, with a stop surface 14 pointing in the propulsion direction V, it is in contact with a counter stop surface 9, pointing opposite the propulsion direction V, of a discharge stop formed by the middle housing section 2. From this zero dose position, the dose to be administered in the next injection is adjusted.

The dose is adjusted through a dosing movement of the dosing member. The dosing movement is a rotation-free translational motion against the propulsion direction V, in the exemplary embodiment, an axial linear movement, as is usual with injection pens in general. Within the limits of the dosing movement, the dosing member can be moved out of the zero dose position up to a proximal stop position. In the proximal stop position the dosing member assumes a maximum dose position, from which, for a subsequent injection, it is again moved away up to the counter stop surface 9 of the distally opposite-lying discharge stop. In the maximum dose position the dosing member, with a stop surface 15 pointing against the propulsion direction V formed by the carrier 12, is in stop contact against a counter stop surface 16 pointing in the propulsion direction V, which the proximal sleeve section 3 forms at a forward front side. The maximum path length of the dosing movement, i.e., the path length from the zero dose position to the maximum dose position is indicated by L. Accordingly, the maximum workable discharge stroke length for the product discharge during the injection also has the length L. The dosing movement and also the discharge movement of the dosing member are thus provided in each case with a hard stop formed by the housing, for one the stop surface 9 and for the other the stop surface 16.

In the zero dose position, the dosing member is in a catch engagement with the housing, in the exemplary embodiment with the proximal sleeve section 3. For the injection device of the first exemplary embodiment, which enables only the repeated adjustment for an always equal dosage, namely the dose designated as maximum dose, defined priming is made possible through the catch engagement. By means of the catch engagement a priming position can be defined between the zero dose position and the maximum dose position up to where the dosing member can execute a short dosing movement. In this sense, the catch engagement, during the simple execution of the injection device of the first exemplary embodiment, forms a dosing catch engagement. The priming position is defined by an increase of the force that must be applied during the dosing movement if the dosing member is to be moved relative to the advancing mechanism past the priming position into the maximum dose position. Within this distance of the path, which extends from the zero dose position to priming position, the force to be applied for this part of the dosing movement corresponds to the elastic restoring force out of the engagement of the carrier 12 in the tooth rows 11 of the piston rod 10. Upon reaching the priming position, the dosing member comes into stopping contact against a catch surface of the sleeve section 3, the surface pointing in the direction of the propulsion direction V. The catch surface is an integral component of the sleeve section 3, the sleeve section 3 forming the catch surface in its sleeve jacket. The catch surface is the proximal boundary wall of a cutout 17, which penetrates the sleeve section 3 radially to the longitudinal axis C. The catch surface of the cutout 17 points radially to the longitudinal axis C.

The sleeve section 3 guides axially the carrier 12 in a distal section and the dosing knob 20 in a proximal section and, thus, the entire dosing member axially. With the exception of the cutout 17, the sleeve section 3 exhibits in its two sections guiding the dosing member 1, a smooth jacket inner surface, which in both sections is preferably circularly cylindrical, if need be with the exception of a straight guide for the dosing member. The sleeve section 3 tightly surrounds the dosing head 20 over its entire circumference that does not protrude from the housing, so that the measured thickness of the sleeve section 3 radially to the longitudinal axis L can be kept low.

The cutout 17 forms a first catch mechanism. A second catch mechanism, which compliments or cooperates with the first catch mechanism to form a catch engagement, is formed at the dosing knob 20 of the dosing member and includes a catch element 21 protruding into the cutout 17 in the catch engagement. The catch element 21 is a lobe projecting outwards radially from a flexible tongue. The catch element 21 and the flexible tongue comprise the second catch mechanism. One embodiment of the catch mechanisms participating in the catch engagement and their cooperation, is depicted in FIGS. 2 through 7.

Figure 2:
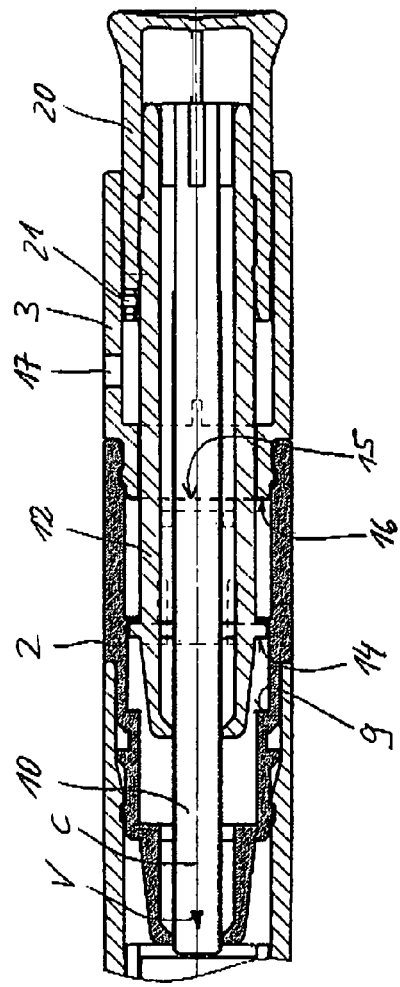
FIG. 2 shows the injection device of FIG. 1 in a state in which a dosing member of the injection device assumes a maximum dose position.

FIG. 2 shows the injection device in a state in which the dosing member has assumed the maximum dose position. The proximal part of the injection device is represented. In the maximum dose position, the catch engagement is released. The catch element 12 presses against the smooth jacket inner surface of the sleeve section 3.

Figure 5:
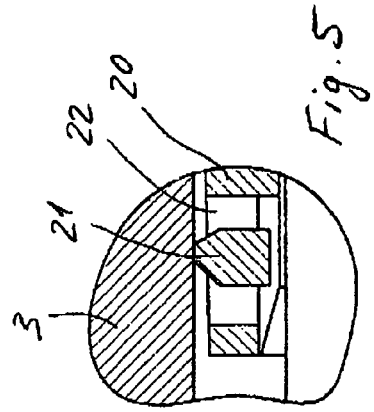
FIG. 5 shows a catch mechanism of the dosing member in detail in the maximum dose position.

The catch element 21 and a section of the surrounding sleeve section 3 in the maximum dose position are presented in FIG. 5 in an enlargement. The flexible tongue carrying the catch element 21 is indicated at 22. It projects in the propulsion direction V from a front face of the dosing knob 20 pointing in the propulsion direction V and carries in the propulsion direction V the catch element 21 spaced away from the front face of interest of the dosing knob 20. In the maximum dose position, the flexible tongue 22 is bent elastically radially inward with respect to its relaxed state, so that the catch element 21 presses against the jacket inner surface of the sleeve section 3 with the elastic bending force of the flexible tongue 22.

Figure 3:
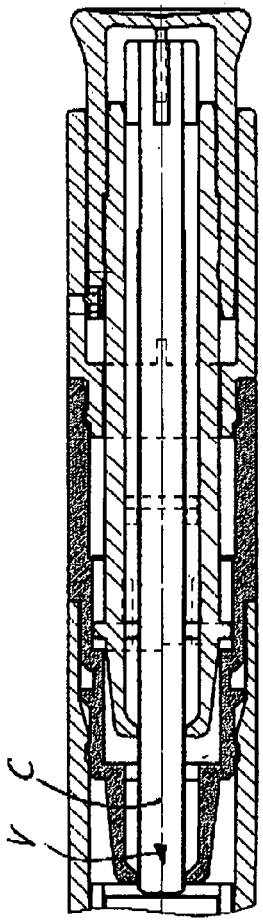
FIG. 3 shows the injection device of FIG. 1 in a state in which the dosing member assumes a priming position.

FIG. 3 shows the injection device in a state in which the dosing member has assumed the priming position.

Figure 6:
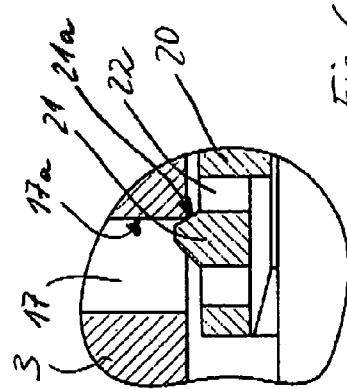
FIG. 6 shows the catch mechanism of the dosing member in the priming position.

The catch engagement in the priming position is depicted in the enlargement of FIG. 6. In the priming position the full catch engagement exists, i.e., the catch element 21 projects maximally into the opening and the flexible tongue is relaxed. The catch element 21 is in the catch position in stopping contact with the catch surface formed by the cutout. The catch surface of the cutout 17 is indicated in FIG. 6 by the reference numeral 17a. While the catch surface 17a radially is simply straight, the catch element narrows to form a counter surface 21a at its free, radially extreme end. In this exemplary embodiment, the counter surface 21a is a flat, radially-inclined diagonal surface on the catch element 21. An outwardly arching form of the stop element for the forming of the counter surface, for example, would also be possible. Instead of providing a sloping or arching for the catch element, such a surface can also be formed at the catch surface 17a.

Figure 4:
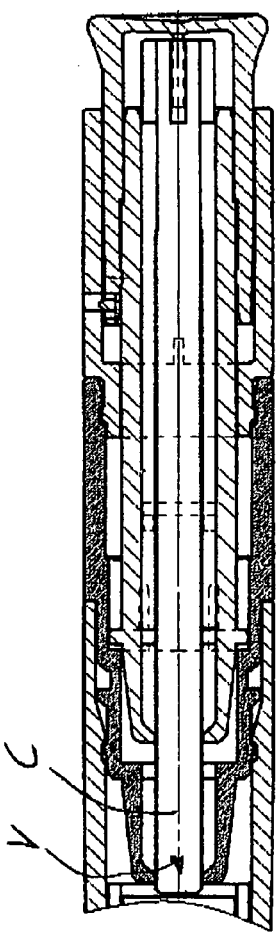
FIG. 4 shows the injection device of FIG. 1 in a state in which the dosing member assumes a zero dose position.

FIG. 4 shows the injection device in a state in which the dosing member has assumed the zero dose position.

Figure 7:
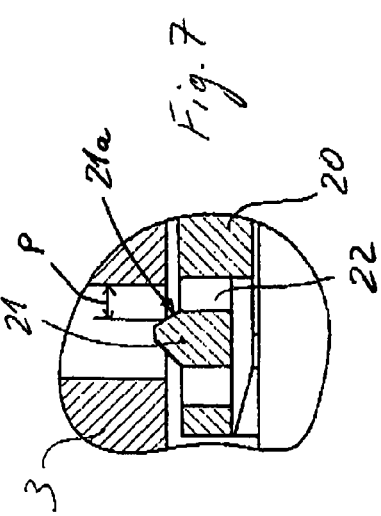
FIG. 7 shows the catch mechanism of the dosing member in the zero dose position.

FIG. 7 shows, in enlarged form the region of the catch engagement for the zero dose position. The catch element projects freely into the cutout 17, i.e., the flexible tongue 22 is relaxed. In contrast to the priming position the catch element exhibits, however, a clear distance p, measured in the forward driving position V, from the catch surface 17a. With the flexible tongue 22 relaxed, the dosing member can be moved within the cutout 17 over this clear distance p against the propulsion direction V up to the clear surface 17a. This small part of the dosing movement is predetermined through the engagement of the carrier 13 in the tooth rows 11 of the piston rod 10. Thus, the clear distance can, in particular, be dimensioned such that the dosing member can be moved from the zero dose position several small tooth gap of the tooth rows 11 along the piston rod 10, for example by 2, 3 or 4 tooth gaps, whereby the distance between each two successive tooth gaps corresponds to a dose unit, in the case where the two tooth rows 11 both exhibit their tooth gaps at the same axial height. Through an axial displacement of the tooth rows 11 and, if need be, through additional axially displaced tooth rows, the dose can again be refined or further adjusted.

FIGS. 8, 9 and 10 each show the injection device in the same view from outside onto the cutout 17. FIG. 8 represents the state corresponding to that of FIGS. 2 and 5, i.e., the dosing member has assumed the maximum dose position. In FIG. 9 it has assumed the priming position and, in FIG. 10, the zero dose position. In the priming position and in the zero dose position the catch element 21 is visible from the outside through the cutout 17. In the maximum dose position it is covered by the jacket of the sleeve section 3. In this way an optical indication of the dose position is also given at the same time. A particular advantage of this dose indicator is that the catch element 21 determining the priming position itself forms part of the indicator. It is further advantageous when the catch element, at its visible end pointing radially outward and visible through the cutout 17, is provided with a marking, e.g., a special color marking, for improvement of the identification by sight, which marking clearly distinguishes it from the sleeve section 3 and, if necessary, from the background recognizable through the cutout 17.

In the case of a first use or after an exchange or a refill of the reservoir 4, the first injection after putting on the cannula holder holding the injection cannula 7 can be performed as follows:

The injection device is in the state of FIG. 1. The dosing member is in the zero dose position.

Before the first injection, a priming step is undertaken. For this, the dosing member is grasped by the dosing knob projecting from the housing and withdrawn relative to the housing and the advancing mechanism to the priming position shown in FIGS. 3 and 6. With this dosing movement, upon reaching the priming position, an increase of force required for a further withdrawal can be clearly felt. This increase in force arises form the fact that the catch element, in the priming position, has come into stopping contact against the catch surface 17a and a further withdrawal of the dosing member is only possible against the elastic force of the flexible tongue 22. The counter surface 21a of the catch element 21 facing the catch surface 17a is formed such that, on the one hand, a self-locking is avoided with certainty, but on the other hand the force increase required to overcome the resistance takes place not gradually but suddenly. The form of the catch element and the elastic force generated by the flexible tongue 22 are appropriately matched to each other.

The reaching of the priming position is clearly visible through the cutout 17. Advantageously, in the zero dose position the proximal region of the catch element visible through the cutout is clearly distinguishable from an adjacent region that also is still visible through the cutout in the priming position, for example, through a different coloring of the two regions. Instead of this or in combination with the coloring, the contour of the catch element visible through the cutout can also contribute to the distinguishing.

After the dosing member has assumed the priming position, the injection cannula 7 is opened by removal of the two protective caps. Subsequently, the dosing member is moved in the propulsion direction V (which also may be thought of as the injection, administration, ejecting, discharge or dispensing movement or direction) through manual force on the dosing knob 20. In this movement, the dosing member takes the advancing mechanism along in the propulsion direction, due to the tooth engagement of the carrier 12 in the tooth rows 11, and product and, as the case may be, air present in the reservoir 4 are forced out of the reservoir 4. The priming stroke executed in the scope of this movement corresponds to the clear distance p that the catch element has in the zero dose position from the stop surface 17a of the sleeve section 3. The clear distance p, i.e., the priming stroke, is dimensioned such that any residual air is removed with certainty from the reservoir 4, but, on the other hand, the least possible medicament is lost. Fluid exiting at the injection cannula 7 signals that the product-carrying parts of the injection device from the reservoir 4 to the outlet of the injection cannula 7 are completely cleared of air. At the same time this sight control offers a certain assurance of the normal functioning of the injection device. During the priming, the injection device should be held so that the injection needle 7 is pointed upward.

After execution of the priming stroke, the injection device is ready for the adjustment (or selection of ) and administration of a dose. In particular, the dosing member assumes the zero dose position after execution of the priming stroke.

For the adjustment of the dose to be administered, the user again pulls the dosing member at the dosing knob 20 in the direction opposite the propulsion direction V, but this time until reaching the fixed end stop 16, so that the dosing member assumes the maximum position. The dosing movement is a linear movement against the propulsion direction V.

With the dosing member in the maximum dosing position, the injection cannula 7 is introduced through the skin up to the subcutaneous tissue. After the desired penetration depth is achieved, the dosing member is pressed in the propulsion direction V into the housing until it is against the stop surface 9 of the discharge stop. This corresponds to the maximum ejection stroke L. With this ejection stroke L the dosing member again takes the advancing mechanism along in the propulsion direction V, and the dose corresponding to the maximum ejection stroke L is ejected and administered.

For additional injections, no further priming is needed until the next replacement of the reservoir 4 or a refilling. Rather, adjustment of the dose can be undertaken directly by transferring the dosing member out of the zero-dose position into the maximum dose position. It is preferred, however, for safety reasons that the user carry out a new priming before each injection. Priming is advantageous not only in the case of a reservoir replacement. Even without a reservoir replacement, another priming after a first priming can be advantageous or required in order to expel air that can have infiltrated, for example because of variations in temperature.

In a likewise preferred embodiment, the catch surface 17*a* blocks the catch element, which is here modified since it does not display the diagonal surface 21*a*, being rather provided with an essentially perpendicularly directed surface with respect to the retracting direction. Elastic deflection solely because of a withdrawal force acting in the retracting direction is thereby prevented. To the contrary, in the priming position, the modified catch element forms a solid stop, whereby maximum safety is obtained for it, which actually is no longer adjusted as the desired priming dose. In order to be able to adjust the dose for dispensing, the modified catch element is elastically pliable and is movable out of the stop with the catch surface 17*a* by actuation from outside, preferably by pressing in.

FIG. 11 to 20 show a second exemplary embodiment of an injection device in accordance with the present invention that is different from the first embodiment, in reference to the first catch mechanism formed by the sleeve section 3. With exception of the first catch mechanism and a dosage scale, the sleeve section 3 is not different from the sleeve section 3 of the injection device of the first embodiment. Different features of the embodiments will be set forth in the following; relative to commonalities, reference will be in common.

The first catch mechanism includes, in the second embodiment, several cutouts in the jacket of sleeve section 3, so that different doses can be set through the dosing catch engagement of the dosing member with the sleeve section 3, and are administered with the injection device.

The first catch mechanism formed by the sleeve section 3 is formed from the same cutout 17 as in the first embodiment, and additional cutouts 18 in the jacket of the sleeve section 3. The cutout 17 is the foremost in the propulsion direction V, i.e., most distal of the cutouts 17 and 18. The cutouts 17 and 18 are in alignment behind one another in the propulsion direction, and formed as perforations and spaced in the jacket of the sleeve section 3. The cutouts 18 and the catch surfaces 18*a* formed from each of these cutouts 18 are identical. Furthermore, the cutouts 18 are different from the cutout 17 only by the fact that the cutouts 18 do not take over any priming function and, correspondingly, are axially shorter than the cutout 17 by the amount of open priming space. Furthermore, also provided for the maximum dose position, which is represented in FIGS. 12 and 15, is a cutout 18 in which the catch element 21 engages in the maximum dose position in order to establish for the user for each of the discretely adjustable doses the same "setting feel."

Because of the plurality of adjustable doses for ejecting, the injection device of the second embodiment displays a dose scale as the additional difference from the first embodiment. The dose scale is mounted, clearly legible, on the sleeve section 3, directly next to the cutouts 17, 18.

FIG. 18 to 20 each show a view onto the cutouts 17 and 18 and the dose scale. FIG. 18 shows the dosing member in the maximum dose position corresponding to FIGS. 12 and 15. FIG. 19 shows the injection device in an intermediate position of the dosing member. Here, each catch engagement in one of the cutouts 18 ahead of the most proximal cutout 18 is understood as an intermediate dose position. In FIG. 19, the dosing member assumes an intermediate dose position in which it engages in the cutout 18 following cutout 17. As an example, the dose scale marks for this intermediate dose position 20 dose units. FIG. 20 shows the injection device in the zero dose position of the dosing member, which it also assumes in FIGS. 11, 14 and 17. The dose scale marks the zero position by the numeral 0. The priming position is identified on the catch surface 17*a* of the cutout 17 with the numeral 4, whose marker stripe is flush with the catch surface 17*a*, while the marker stripe going out from the 0 is away from, the catch surface 17*a* by the priming interval p.

The injection device of the first embodiment could also display a similarly constructed dose scale, where, however, its dose scale would include only the dose numbers for the zero dose position and the priming position. Instead of giving a number, the letter p (for priming) could be used for the priming position in the first as well as in the second embodiment.

As with the catch element 21 of the first embodiment, the catch element 21 of the second embodiment is also provided, on its side pointing in the propulsion direction V, with another diagonal surface 21*b*. While the diagonal surface 21*b* in the case of the first embodiment fulfills no function, in the second embodiment it facilitates propulsion of the dosing member when ejecting by preventing blocking. Alternatively, diagonal surfaces could be provided in each of the limiting, oppositely lying front walls of the cutouts 17 and/or 18. The diagonal surface 21*b* could, instead of flat, also be arched, preferably outwardly arched. The same applies for sliding surfaces that can be formed in the cutouts 18.

FIG. 21 to 26 show another exemplary embodiment of an injection device in accordance with the present invention. This embodiment is different from other embodiments relative to the first catch mechanism and also relative to the second catch mechanism, i.e., to the catch engagement as such. However, aside from the catch mechanisms and the catch engagement, the injection device again corresponds to the injection devices of the other two embodiment so that, relative to this, reference will be made to the description of the first embodiment.

Figure 21:
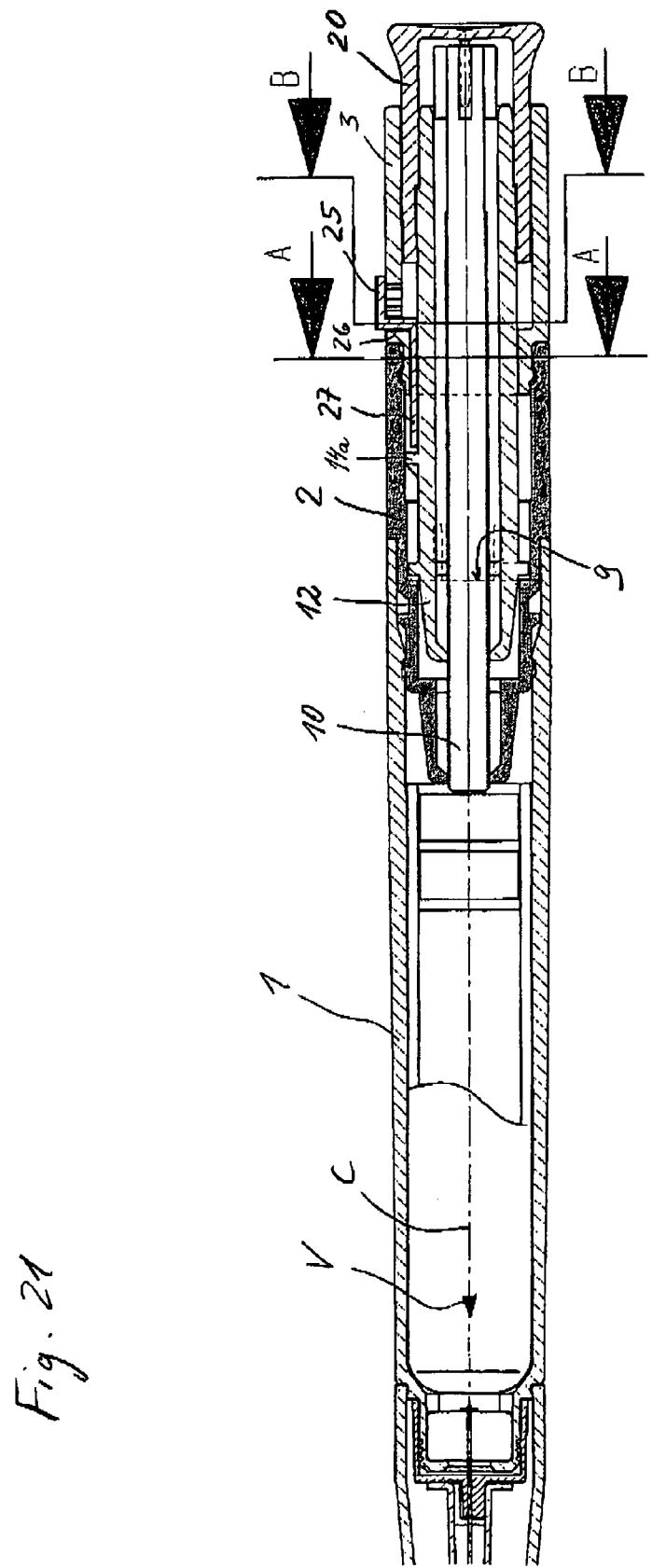
FIG. 21 shows an injection device according to another exemplary embodiment.
Figure 24:
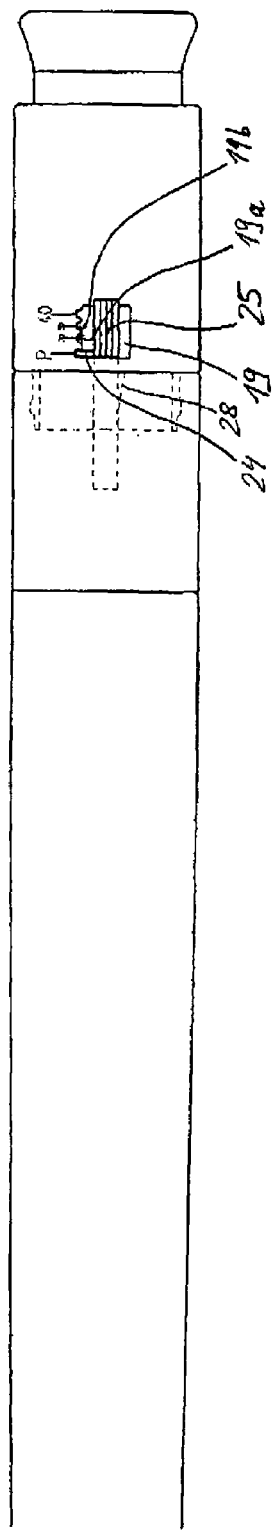
FIG. 24 shows the injection device of FIG. 21 a plan view of a catch mechanism of a housing of the injection device, wherein the dosing member assumes the zero dose position.
Figure 25:
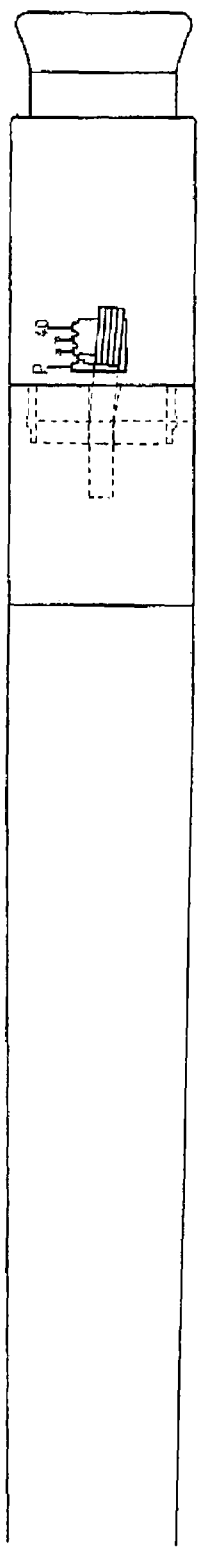
FIG. 25 shows a plan view of FIG. 24, wherein the dosing member assumes an intermediate position.
Figure 26:
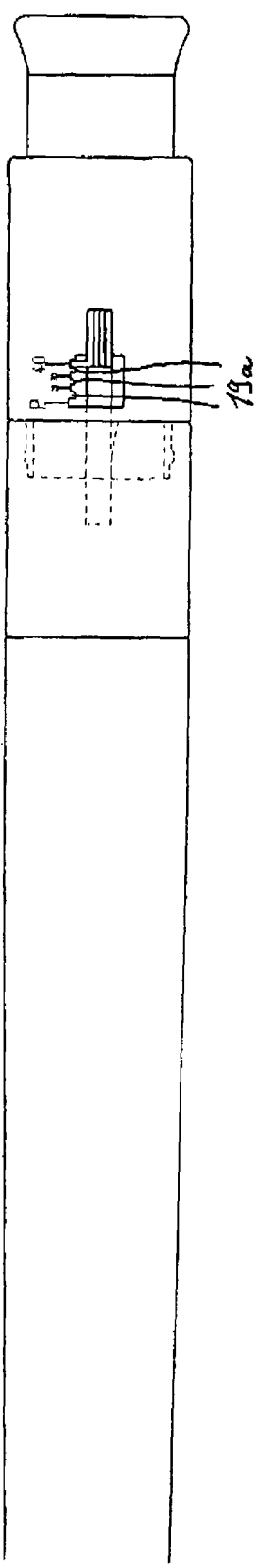
FIG. 26 shows a plan view of FIG. 24, wherein the dosing member assumes the maximum dose position.

One difference from the previously described embodiments is that the catch engagement is produced not by a radial snap movement, but rather in a snap movement directed in the circumferential direction of the sleeve section 3 of the second catch mechanism, and is released by a corresponding counter movement. Further, the dosing knob 20 does not form the catch mechanism in a single piece. The second catch mechanism is formed by means of a separate dosing catch body that is inserted between the sleeve section 3 and the carrier 12, in a cutout formed by the sleeve section 3. To be recognized from the single piece dosing catch body, in the longitudinal section of FIG. 21, are the catch body parts 25, 26 and 27. FIG. 24 to 26 further show a catch element 24 projecting away from the catch body part 25 in the circumferential direction of the sleeve section 3. FIGS. 22 and 23 further show the two cross sections A—A and B—B sketched in FIG. 21. In the following description of the injection device of this embodiment, reference may be made to FIG. 21–26.

In the assembled condition, the dosing body displays a straight, axially extending connecting part 27, a connecting part 26 projecting away from here radially outwardly at a proximal end, a retaining part 25 projecting away from the connecting part 26 axially in the proximal direction, and the catch element 24 formed in the manner of a lobe projecting away from the retaining part 26 in the circumferential direction of the sleeve section 3. As can be recognized by viewing FIG. 21 to 23, together, the sleeve section 3 displays an axially extended cutout 28 in a distal sleeve region on the sleeve inner surface tightly enclosing the lobe 12, in which the connecting part 27 of the catch body (comprising catch element 24, retaining part 25, connecting part 26 and connecting part 17) is guided axially straight. The cutout 28, in a proximal end section, widens in the circumferential direction of the sleeve section 3. The connecting part 27 is guided straight further in the end section on a first of its two perimeter sides. On the other second perimeter side of the connecting part 27 there remains a space in the end section of the cutout 28 that enables elastic yielding of the connecting part 27 in the circumferential direction. In a distal region of the cutout 28, the connecting part 27 is firmly enclosed in the cutout 28 in both circumferential directions, so that there exists there a firm clamping for the elastic transverse beam formed from the connecting part 27. The lobe 12 and the catch body can be moved relative to one another in or opposite the propulsion direction.

The retaining part 25 of the catch body projects outwardly over the sleeve section 3 of the housing so that the catch body for disengaging the dosing catch engagement is actuated, namely can be elastically arched out from the catch engagement in the circumferential direction.

The first catch mechanism is again formed, like in the case of the injection devices of the other exemplary embodiments, in a cutout 19 directly through the jacket of the sleeve section 3. However, in the third embodiment, the first catch mechanism does not form a proximal limiting wall of the cutout 19, but rather a limiting wall extended axially, pointing in the direction of the periphery. Formed on this limiting wall in the propulsion direction V behind one another are stop surfaces 19a and 19b, each in a number that, as in the case of the second embodiment, corresponds to the number of doses that can be set. The limiting wall is formed like a comb, whereby the teeth of the comb project out in the circumferential direction, and are arranged spaced apart axially behind one another. The surfaces of the teeth pointing in the propulsion direction V form the catch surfaces 19a and the teeth surfaces pointing against the propulsion direction form the catch surfaces 19b of this first catch mechanism. Placed centrally in the valleys between the teeth are marker stripes of a dose scale and a dose number.

FIGS. 21 and 24 show the dosing member in the zero dose position. In this position, the catch element 24 engages in the distal comb base. FIG. 26 shows the dosing member in the maximum dose position, in which the catch element 24 engages in the most proximal comb base.

FIG. 25 shows the injection device in the same view as FIGS. 24 and 26, however during the dosing movement of the catch body out of the zero dose position into the maximum dose position. The front and back side of the catch element 24 and also those of the catch surfaces 19a and 19b formed from the teeth of the comb are formed such that a dosing movement of the dosing member is possible only by actuation of the catch body.

The axial position of the catch body determines the dose. In order to adjust the dose, the catch body is arched out of the catch engagement in the circumferential direction of the sleeve section 3, against its elastic restoring force, and moved axially into the desired catch position. Because of the catch engagement in which the catch body is fixed axially on the sleeve section 3, the stop member forms in the stop position a dosing stop for the dosing member when it executes its dosing movement directed opposite to the propulsion direction V. Acting as a stop pair are a distal front surface of the catch body as a dosing stop and a lobe 14a of the dosing member projecting transversally to the propulsion direction V. The ejecting movement of the dosing member, as in the case of the other exemplary embodiments, is limited by an ejecting stop.

For priming, the catch body is set in its most distal catch position. The dosing member is moved away from the ejecting stop 9 opposite to the propulsion direction V up to or against the dosing stop of the catch body, and can next be moved from the dosing stop by the amount of the short priming stroke up to against the ejecting stop 9.

Outlined along the first catch mechanism is a dose scale that extends from a minimum dose "P" up to a maximum dose (FIG. 24–26). The minimum dose corresponds to the priming dose. The axial distance from one another that the ejecting stop 9 and the most distal catch position of the second catch mechanism display is selected correspondingly. By splitting the dosing device into the dosing member and the separate dosing catch body, the dosing is also split, namely into a selection movement of the catch body and a retracting movement of the dosing member against the dosing stop of the catch body. But the selection movement, aside from the required stopping, is an axial movement, as is the retracting movement of the dosing member.

In the foregoing description, embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. An injection device, comprising:
a) a housing having a longitudinal axis;
b) a reservoir positioned within the housing and containing a product to be injected;
c) an advancing apparatus that carries out an advancing movement in order to advance an adjusted product dose from the reservoir;
d) a dosing member that carries out a propulsion movement relative to the housing in a propulsion direction and a dosing movement counter to the propulsion direction, said dosing member coupled with the advancing apparatus such that the propulsion movement causes the advancing movement of the advancing apparatus;
e) a first catch mechanism formed in the housing; and
f) a second catch mechanism formed on the dosing member and adapted to releasably engage the first catch mechanism
g) wherein the adjusted product dose is selected and set prior to injection of the product via a non-rotational dosage selecting and setting movement of sliding the dosing member along the longitudinal axis of the housing until the second catch mechanism engages with the first catch mechanism.

2. The injection device according to claim 1, wherein the first catch mechanism is not pliant.

3. The injection device according to claim 1, wherein the first catch mechanism forms at least one catch surface pointing in the propulsion direction, and, when engaged with the first catch mechanism, the second catch mechanism grasps behind the at least one catch surface.

4. The injection device according to claim 3, wherein the housing comprises at least one perforation and a boundary wall of the perforation forms the at least one catch surface.

5. The injection device according to claim 4, wherein a proximal boundary wall of the perforation forms the at least one catch surface.

6. The injection device according to claim 1, wherein a catch element of the second catch mechanism is visible from the outside through the housing.

7. The injection device according to claim 6, wherein the catch element is visible through the housing only in the catch engagement.

8. The injection device according to claim 1, wherein the first catch mechanism comprises several catch surfaces arranged in a row in the propulsion direction, which surfaces can each be brought into a catch engagement with the second catch mechanism in order to be able to set different doses.

9. The injection device according to claim 8, wherein the housing is provided with several cutouts arranged in a row in the propulsion direction and each one of the cutouts forms one of the catch surfaces.

10. The injection device according to claim 1, wherein the second catch mechanism is elastically pliant for the releasing from the first catch mechanism.

11. The injection device according to claim 10, wherein the second catch mechanism includes a flexible tongue and a catch element that projects from the flexible tongue and engages the first catch mechanism.

12. The injection device according to claim 10, wherein the second catch mechanism, relative to a central longitudinal axis of the housing, snaps radially outward, thereby engaging the first catch mechanism.

13. The injection device according to claim 10, wherein the second catch mechanism snaps into the first catch mechanism in a peripheral direction of the housing.

14. The injection device according to claim 1, wherein, when the second catch mechanism is engaged in the first catch mechanism, the dosing member can carry out a priming movement relative to the housing and relative to the advancing apparatus, the distance of which priming movement is shorter than a maximum distance of the dosing movement.

15. The injection device according to claim 1, wherein, in a first dose position of the dosing member, in which a catch element of the second catch mechanism grasps behind a catch surface, pointing in the propulsion direction, of the first catch mechanism, a clear gap remains in the propulsion direction between the catch surface and the catch element, which gap is substantially smaller than a maximum distance of the dosing movement, so that the dosing member in the catch engagement can carry out a short dosing movement for a priming.

16. The injection device according to claim 1, wherein the advancing apparatus comprises a piston in the reservoir and a piston rod, and the dosing member is operably coupled with the piston rod.

17. An injection device, comprising:
a housing for receiving a reservoir of liquid to be dispensed; and
a dispensing apparatus positioned within the housing and movable along a longitudinal axis of the housing;
wherein the housing includes a first catch mechanism and the dispensing apparatus includes a second catch mechanism adapted to releasably engage the first catch mechanism of the housing, and
wherein the dispensing apparatus enables dispensing of a dose of liquid from the reservoir when slid a predetermined distance along the longitudinal axis of the housing in a dispensing direction, and the dispensing apparatus enables non-rotational selection of the predetermined distance prior to dispensing the liquid by sliding the dispensing apparatus along the longitudinal axis of the housing in a direction generally opposite to the dispensing direction until the second catch mechanism engages with the first catch mechanism, thereby enabling selection of the dose of liquid to be dispensed.

18. The injection device of claim 17, wherein the first catch mechanism comprises several catch surfaces arranged in a row in the dispensing direction, which surfaces can each be brought into a catch engagement with the second catch mechanism in order to be able to set different doses.

19. The injection device of claim 17, wherein, when the second catch mechanism is engaged in the first catch mechanism, the dispensing apparatus can carry out a priming movement by sliding the dispensing apparatus in the dispensing direction for a priming distance that is shorter than the predetermined distance.

* * * * *